United States Patent [19]

Kelen

[11] Patent Number: 5,092,341
[45] Date of Patent: Mar. 3, 1992

[54] SURFACE ECG FREQUENCY ANALYSIS SYSTEM AND METHOD BASED UPON SPECTRAL TURBULENCE ESTIMATION

[75] Inventor: George J. Kelen, Staten Island, N.Y.

[73] Assignee: Del Mar Avionics, Irvine, Calif.

[21] Appl. No.: 539,581

[22] Filed: Jun. 18, 1990

[51] Int. Cl.⁵ .................................................. A61B 5/045
[52] U.S. Cl. .................................. 128/702; 364/413.06
[58] Field of Search ............... 128/696, 702, 703, 704, 128/705, 710; 364/413.06

[56] References Cited

U.S. PATENT DOCUMENTS

| | | | |
|---|---|---|---|
| 3,884,221 | 5/1975 | Eastman | 128/699 |
| 4,630,204 | 12/1986 | Mortara | 128/696 |
| 4,680,708 | 7/1987 | Ambos et al. | 128/702 |
| 4,924,875 | 5/1990 | Chamoun | 128/702 |
| 4,947,857 | 8/1990 | Albert et al. | 128/696 |
| 4,961,428 | 10/1990 | Nikias et al. | 128/699 |

OTHER PUBLICATIONS

Instantaneous power spectra by Chester H. Page, Jan. 1952, pp. 103-106, Journal of Applied Physics.
Introduction to EEC Spectral Analysis by Sciarreta and Erculiani, 1977, the entire book.

*Primary Examiner*—William E. Kamm
*Attorney, Agent, or Firm*—Derrick M. Reid; James D. Leimbach; W. D. English

[57] ABSTRACT

Frequency domain ECG signal processing systems and methods plot spectral maps and compute statistical parameters from surface electrocardiographic signals, which plots and parameters reveal abnormalities of electrical conduction within the hearts of patients at risk of ventricular tachycardia. Fourier analysis of short overlapping time segments of QRS ECG signal are used to create three dimensional spectral maps disclosing changes in the frequency spectral content of the ECG signal over the whole QRS region. Correlations and statistical evaluations of the spectral content between QRS time segment pairs quantify the spectral turbulence of the ECG and distinguish those at risk from ventricular tachyarrhythmias.

35 Claims, 7 Drawing Sheets

SURFACE ECG FREQUENCY ANALYSIS SYSTEM AND METHOD BASED UPON SPECTRAL TURBULENCE ESTIMATION

RELATED PATENT APPLICATION

This application is related to companion patent application entitled Method and Apparatus for Spectral Analysis of Electrocardiographic Signals, Ser. No. 07/496,976, filed Mar. 19, 1990, naming the same inventor of the present application and naming the same assignee of the present application.

BACKGROUND OF THE INVENTION

1. Field of the Invention

This invention relates to methods and devices for analysis of the electrical activity of the heart (Electrocardiography) and more particularly to the field known as High Resolution Electrocardiography, which is concerned with detecting abnormalities not apparent on conventional electrocardiograms. The specific and major purpose intended for the present invention is the clinical evaluation of medical patients for risk of life-threatening arrhythmias of the heart. However, both the method and apparatus are potentially suitable for research into and diagnosis of a wide variety of other disorders of cardiac electrical activity, and the analysis of other bioelectrical signals such as those recorded on an Electroencephalogram (EEG).

2. Description of the Prior Art

In order to fully comprehend the purpose and method of the present invention, it is necessary to be familiar with certain standard physiological and electrocardiographic (ECG) nomenclature. Relevant portions of that nomenclature are briefly summarized here for the benefit of the reader not conversant with medical terminology.

The pumping action of the normal heart results from the orderly contraction of millions of individual muscle cells. Each heart beat is initiated by the spontaneous periodic activity of certain specialized cells of a structure known as the sino-atrial node. Activation of heart muscle cells is initiated by an electrical pacing signal generated in the sino-atrial node and propagated by specialized tissues known collectively as "the conducting system" of the heart. At the cellular level, the process of activation is known as "depolarization" because it involves transient changes in the electrical potential across the cell membrane mediated by the passage of ions. The process of recovery to the normal resting state is referred to as "repolarization".

The spread of the wavefront of electrical depolarization through the atria, that is the "primer pumping chambers" of the heart, gives rise to the deflection on the electrocardiogram known as the P wave. Contraction of the main cardiac pumping chambers, that is the ventricles of the heart, is associated with a multiphasic deflection of the ECG waveform known as the QRS complex. Spread of the wavefront of electrical recovery (repolarization) through the ventricles gives rise to the T wave of the ECG. The time interval between the end of the QRS complex and the T wave, referred to as the ST segment, is normally free from electrical activity, but may harbor small amplitude signals known as late potentials which extend out beyond the end of the QRS complex (as viewed at ordinary magnification) into the ST segment. All of the components of ECG waveforms result from the synchronous spread of electrical signals associated with the activation or recovery of individual cardiac cells, across millions of such cells.

Over fifty-thousand people die annually in the U.S. of unexpected or sudden cardiac death, almost always from a catastrophic failure of normal electrical conduction within the heart known as ventricular fibrillation. Instead of the normal orderly and synchronous contraction of the heart muscle cells necessary for pumping of blood to occur, individual muscle fibers contract in a random and totally disorganized fashion. This arrhythmia (abnormal cardiac rhythm) frequently occurs in association with a myocardial infarction, i.e. a heart attack, either within the first minutes, hours, or sometimes months to years later, but is also the final common pathway for almost all forms of death from cardiac causes. Ventricular fibrillation is a terminal event because no blood at all gets pumped and vital organs such as the brain die from lack of oxygen within minutes unless either the rhythm is corrected, i.e. defibrillated, or the circulation is artificially supported by some other means such as CPR or cardiopulmonary bypass (heart-lung machine).

A frequent immediate predecessor to ventricular fibrillation is another arrhythmia known as ventricular tachycardia (VT) during which, although some blood is pumped, the heart rate is usually too rapid for efficient pumping to occur. The resulting decrease in blood flow may result in symptoms such as loss of consciousness or lightheadedness. VT may spontaneously revert back to a more normal heart rhythm in which case it is referred to as "nonsustained", or it may persist for longer than thirty seconds in which case it is referred to as "sustained". If all QRS complexes during an episode of VT appear similar to each other, the VT is referred to as "monomorphic". Sustained monomorphic ventricular tachycardia (SMVT) has been shown to be closely linked with risk of sudden death in clinical studies.

Despite the existence of a wide variety of more or less successful treatments such as drug therapy, surgery or implantable defibrillators for the prevention or correction of ventricular arrhythmias, their use is not without risk or expense. Classical electrocardiography as practiced for several decades is unfortunately very poor at predicting who is likely to suffer ventricular arrhythmias. Although it is known that increased risk is associated with certain states such as a severely damaged or dilated left ventricle, (the main pumping chamber of the heart), there remains an urgent need for a means of delineating those patients at significant risk, who might truly benefit from aggressive therapies, from amongst the vast majority of potential candidates in whom the risk of life threatening arrhythmia is low and for whom aggressive or expensive therapies may actually do more harm than good. Such an arrhythmia risk screening test should preferably be non-invasive, i.e., not require breaking of the skin surface, and free from risk and discomfort to the patient.

The most reliable method currently available for predicting likelihood of development of a lethal arrhythmia is a diagnostic procedure called electrophysiological study (EP), during which slender wires referred to as pacing catheters are introduced through the skin into a large vein and advanced under X-ray guidance into the heart chambers. Attached to the pacing catheters is a device which generates electrical pulses similar to those produced by a pacemaker. The interior surface of the heart is then subjected to electrical stimulation pulses in an attempt to induce sustained monomorphic ventricular tachycardia. If SMVT is successfully induced, the patient is deemed to be much more likely to spontaneously develop a lethal rhythm disorder. Unfortunately, electrophysiological study is invasive, requires admitting the patient to hospital, is often distressing to the patient who may have to be defibrillated out of a successfully induced arrhythmia, and is time, labor and cost intensive.

Among available non-invasive arrhythmia risk assessment techniques, so-called late potential analysis has received the most attention both in the medical literature and commercial practice. The patents of Simpson, U.S. Pat. No. 4,422,459, Netravali, U.S. Pat. No. 4,458,691, and Strick, U.S. Pat. No. 4,492,235, teach a method currently in widespread use on real-time ECG recorders. Many variants of the method have been advocated in the medical literature. Late potentials are signals of very low amplitude, i.e. less than forty micro volts, versus about one milli volt for the main QRS signal, and, thus require employment of a special noise reduction technique known as signal averaging for such late potentials to be discernible above background noise. Late potential presence beyond the end of the normal QRS 4 complex is about seventy percent predictive for inducibility of SMVT at electrophysiological study and thus predictive of possible serious spontaneous ventricular arrhythmia. However, late potential analysis cannot be used at all in the presence of certain relatively common types of ECG abnormality, and its sensitivity is less than would be desirable.

The Simson patent teaches identification of late potentials by analysis in the time domain only, without any attempt to explicitly analyze their frequency spectral content. Bipolar ECG signals from three orthogonal surface leads are bidirectionally filtered and then algebraically summed into a single vector magnitude upon which certain characteristics of the terminal QRS signal are then measured. Late potentials are deemed to be present or absent depending upon the duration and amplitude of the terminal QRS region. Late potentials are sometimes found by time domain techniques in perfectly normal, healthy patients. The present invention teaches a method which has been shown in clinical studies to be substantially more accurate than late potential analysis at correctly identifying patients in whom SMVT would be inducible at electrophysiologic study, and hence are at increased risk of life- threatening arrhythmia.

The Kelen U.S. Pat. No. 4,883,065, disclosed a system for the analysis of late potentials from long-term recordings of ECGs made on an ambulatory monitor, e.g. a Holter monitor.

The Ambos et al US Pat. No. 4,680,708, teaches a frequency domain technique for late potential identification using Fourier analysis of a single, relatively long segment of ECG signal positioned over the terminal QRS region. Abnormality is allegedly characterized by the presence of secondary high frequency peaks and an excess ratio of high frequencies to low frequencies.

Frequency spectral analysis techniques for ventricular tachycardia risk assessment have, prior to the present invention, used Fourier Analysis of the terminal portion of the QRS complex and early ST segment seeking to identify late potentials by unique frequency spectral content in the form of additional high frequency peaks or abnormal content of high frequencies. These techniques have sought to improve tachyarrhythmia risk detection by better identification of late potentials based upon their putative frequency characteristics. These techniques have been criticized as unreproducible and unconfirmed by independent research. A serious theoretical limitation of late potential analysis arises from the concept that these potentials may represent the visible tip of large but obscured myocardial regions with abnormal activation having most of the electrical activity from such regions buried partially or totally within the QRS complex proper. Partial obscuring of late potentials may occur if the abnormal myocardial region begins to be activated relatively early during the QRS complex, for example, in anterior as compared to inferior wall myocardial infarction. During bundle branch block, myocardial zones with abnormal activation may be totally obscured by the delayed activation of normal myocardial regions. On the other hand, time domain analysis may show late potentials in otherwise normal hearts as a result of applying a high pass filter to a terminal QRS region of lower than normal amplitude or slope due to bundle branch block.

Other limitations of time domain analysis include sensitivity to the specific algorithm used for determining QRS termination, the arbitrary nature of the scoring criteria, and the relatively low predictive accuracy of late potential analysis in the presence of intraventricular conduction defect or bundle branch block. Conventional frequency domain analysis as practiced by the prior art is vulnerable to the duration and the time phase of the analyzed signal as well as to the arbitrary definition of low and high frequency components of the signals.

Hence there exists a need to more accurately predict those at risk from ventricular arrhythmias. The limitations and disadvantages of the prior art are solved or reduced by employing the systems and methods of present invention.

SUMMARY OF THE INVENTION

An object of the present invention is to provide an ECG analysis method and apparatus by which it is possible to accurately identify patients at significant risk of experiencing a serious ventricular arrhythmia.

Another object of the invention is to provide a ventricular arrhythmia risk analysis method and apparatus that does not require invasion of the human body, puncturing of the patient's skin, admission to hospital, or significant risk, pain or discomfort to the patient.

Still another object of the invention is to provide a method and apparatus for frequency analysis of ECG signals that can distinguish and quantify spectral turbulence of the QRS complex as a likely indicator of patients with serious arrhythmia risk.

Still another object of the invention is to provide a method and apparatus for the calculation of numeric parameters which are useful in distinguishing normal from abnormal electrical conduction within the heart.

A further object, is graphic display and hard copy generation of the spectral maps from which the numerical calculations are derived, thus providing both visual qualitative and numerical quantitative methods for classification of recordings.

Still a further object of the invention is to provide a frequency analysis method and apparatus which in its standard default mode of operation performs, upon issue of a single command, analysis according to a fixed predefined stepped signal processing protocol that results without further operator intervention in the generation of visual plots and a numeric report suitable for ventricular arrhythmia risk prediction.

Yet another object of the present invention is provide a system and method for operation in a default routine mode suitable for use by a technician for the routine prediction of patients at risk from SMVT and routine generation of spectral plots for subsequent diagnosis.

Yet a further object of the invention is to provide a frequency analysis method and apparatus having an operator interactive mode of operation whereby the individual steps of the analysis protocol can be customized from a menu, with sufficient flexibility and convenience so as to be suitable for use by researchers seeking to identify improved means of making electrocardiographic diagnoses based upon the visualization and measurement of the frequency characteristics of ECG signals as they change with time.

The present invention follows from a discovery that arrhythmogenic abnormalities are indicated by frequent and abrupt changes in frequency spectrum of the QRS wavefront velocity as it propagates throughout the ventricle around areas of abnormal conduction, resulting in a high degree of spectral turbulence. The analysis of spectral turbulence occurring throughout the entire ventricular depolarization period as taught by the present invention challenges some basic concepts as to the role played by late potentials in the arrhythmogenic process. Spectral analysis as taught by the present invention is an advantage over time-domain late potential analysis for predicting patients at risk from SMVT. The present invention teaches that a high degree of spectral turbulence of the ventricular activation wave front during normal cardiac rhythm reflects the presence of myocardial regions with abnormal conduction characteristics that may provide the anatomic- electrophysiologic substrate for reentrant tachyarrhythmias. The activation of these myocardial regions may occur totally within the QRS complex or may extend beyond the activation of the rest of the ventricular mass. The spectral turbulence generated by the activation wavefront traversing these regions is not obscured by the delayed, possibly slower, but still largely synchronous and uniform activation wavefront in the presence of bundle branch block. Conversely, the delayed but smooth activation process of bundle branch block in normal hearts will not be reflected as a high degree of spectral turbulence. The present invention can be applied to all patients irrespective of QRS duration and the presence or absence of intraventricular conduction abnormality or bundle branch block. Thus, it has been discovered that a high degree of spectral turbulence of the overall QRS signal during sinus rhythm provides a more accurate indication of an anatomic-electrophysiologic substrate for reentrant tachyarrhythmia regardless of the detection of late potentials in the terminal QRS region by either time or frequency domain analysis of the prior art. The present invention employs a new frequency domain analysis system and method which overcomes some of the disadvantages of both time domain late potential analysis and previously advocated methods of frequency analysis of the terminal QRS region, whilst correctly identifying arrhythmogenic risk in patients misclassified or not suitable for analysis by earlier methods.

The frequency domain analysis technique of the present invention is fundamentally different from all others in that it does not rely upon the detection or measurements of late potentials. Observations, measurements and calculations are made instead upon the QRS complex generally as a whole and not upon any portion arbitrarily identified by a temporal, frequency or amplitude characteristic. Further, no assumptions are made as to whether abnormality is represented by abnormally high or abnormally low frequencies, anywhere throughout the whole QRS complex. None of the abnormality criteria invoke any arbitrary value for signal amplitude, duration or frequency.

The present invention thus differs from all methods of the prior art in that it does not attempt to detect, analyze or measure late potentials at all. It does not focus attention on the terminal QRS portion of the ECG signal, but rather evaluates all of the QRS region as a whole, searching for abnormal lack of homogeneity in the frequency spectrum of the signal throughout the time of ventricular depolarization activity.

The present invention teaches among other things, a novel method of distinguishing those patients associated with serious arrhythmia risk based upon frequency spectral content and features of their ECGs. The present invention further teaches spectral mapping of multiple overlapping ECG signal segments, spanning the whole QRS complex, with abnormality recognizable by features of three dimensional maps and computed numeric parameters. The present invention further teaches a system and method for quantifying spectral turbulence of the QRS complex as a whole as the primary indicator of those at risk of SMVT. The novel method and apparatus supports clinical diagnosis via spectral feature analysis and is applicable to the analysis of ECG signals recorded on Holter tapes, as well as upon real time ECG signals.

The present invention comprehends a method and apparatus for performing frequency analysis upon relatively short, stepped but overlapping time segments spanning the whole QRS complex from one or more channels of ECG signal, in combination with pre-processing and post-processing steps appropriate to the intended purpose, to generate three dimensional maps having Time, Frequency and Amplitude axes, reflecting the amplitude and time course of the various frequency spectral components of the ECG signals. From the same frequency spectral data used to generate the maps, calculations are made of various numeric parameters which quantify visually apparent morphological features of the maps, such as contour smoothness and spectral turbulence statistical parameters. The three-dimensional maps, which may be plotted in several different orientations, are combined with a printout of the numeric parameters to generate a report from which both visual morphologic and quantitative assessments of abnormality can be made. Frequency spectral statistical parameters are combined in whole or in part to more accurately predict those at risk from serious ventricular arrhythmias. Furthermore, the present invention provides a scoring system as an accurate indicator for the anatomic-electrophysiologic substrate of reentrant tachyarrhythmias. These and other advantages of the present invention will become apparent to those skilled in the art from the following detailed description of the preferred embodiment.

DETAILED DESCRIPTION OF THE PREFERRED EMBODIMENT

The present invention detects, displays and quantifies abrupt changes in wavefront velocity as the ventricular activation wavefront traverses regions with abnormal conduction characteristics by spectral analysis of the body surface QRS complex. Some abnormal patients have moderately severe spectral turbulence throughout the QRS complex, while other abnormal patients may have even greater spectral turbulence but localized to only a portion of the QRS complex. Hence, four statistical spectral turbulence parameters: low intersegment correlation ratio, intersegment correlation mean and intersegment correlation standard deviation, and spectral entropy, have been developed in order to optimally detect these sub-classes of spectral turbulence occurring anywhere throughout the whole QRS region. The four parameters are finally combined into a single abnormality score so that the medical practitioner can have a simple quantified basis to aid diagnosis. The invention includes a method for summing these four statistical spectral turbulence parameters by statistical normalization. Each of the four parameters is either a zero or a one for normal or abnormal, respectively, so that total scores may range between zero and four. A cumulative score of zero to two was found to be normal and three to four was found to be abnormal in a large clinical study. In addition to the four statistical measures of spectral turbulence specifically noted above, which have already been shown in a clinical study to have superior diagnostic accuracy compared to techniques of the prior art, several additional numeric parameters of theoretical merit are provided in the preferred embodiment of the invention, along with the ability to perform conventional prior art time domain and frequency analysis.

Figure 1:
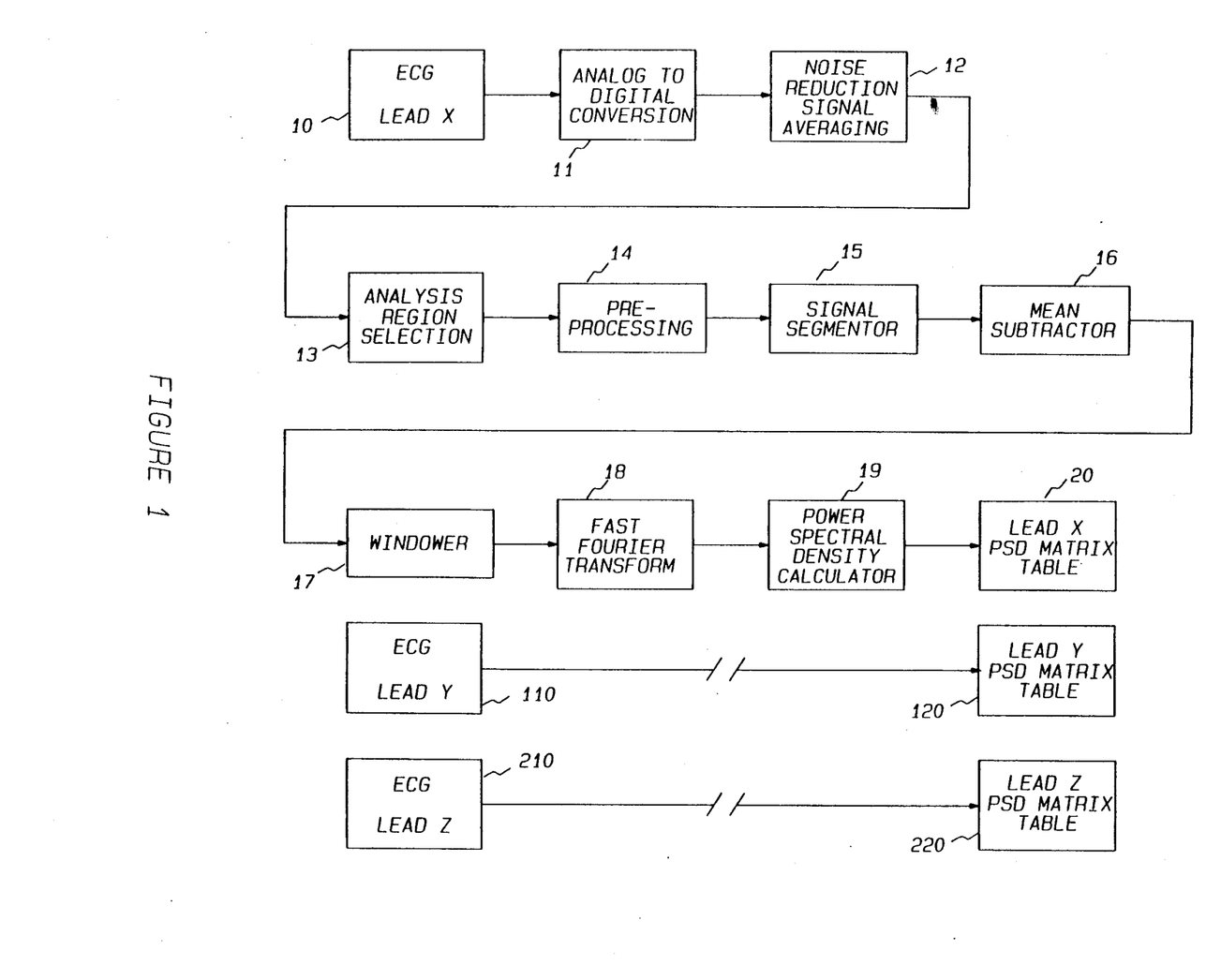
FIG. 1 is a block diagram of a means for generating power spectral density (PSD) matrices for subsequent spectral analysis from three leads X, Y and Z of electrocardiographic signals.
Figure 2:
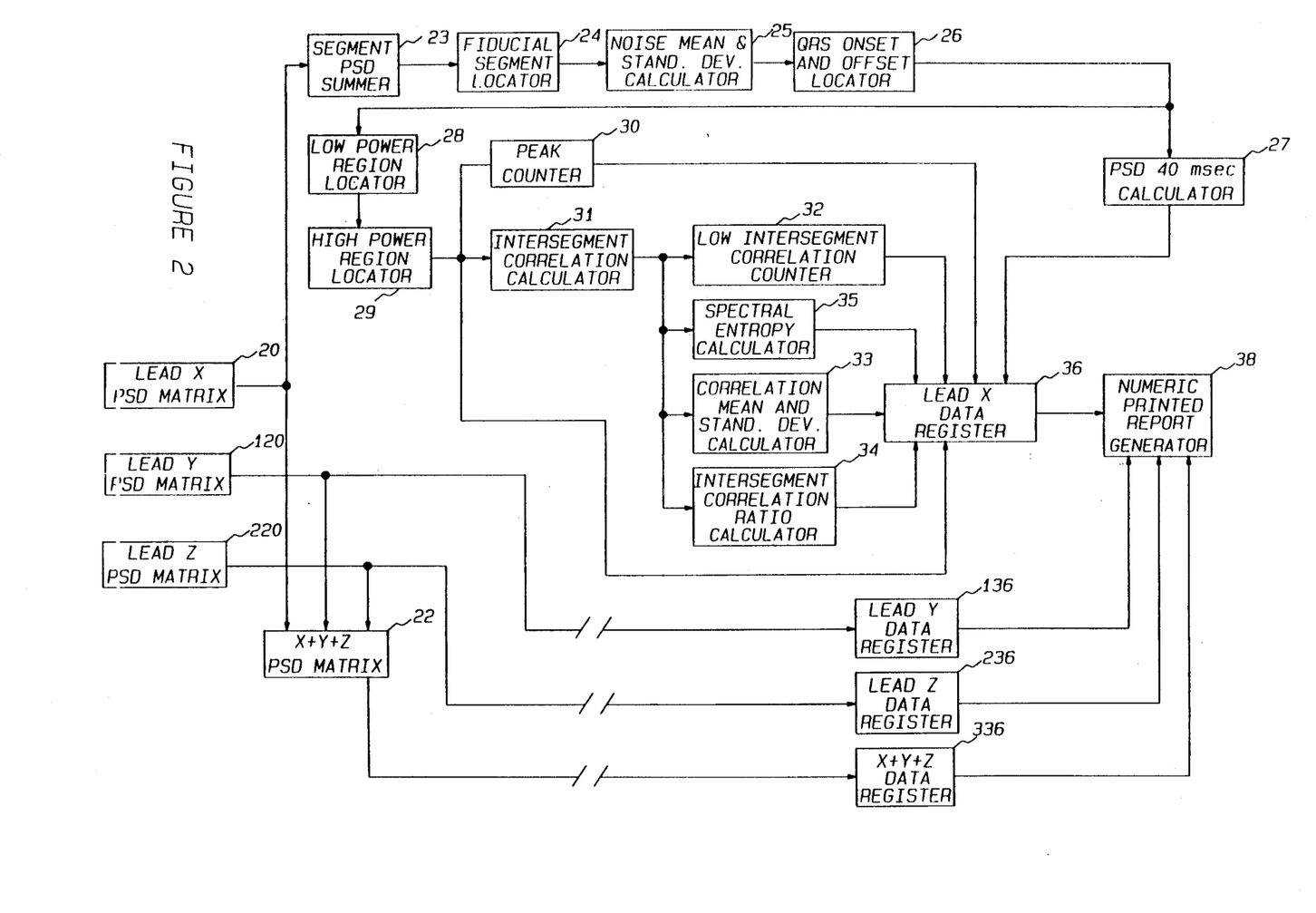
FIG. 2 is a block diagram of a means in the preferred embodiment for generating spectral turbulence statistical parameters from the PSD matrices.
Figure 3:
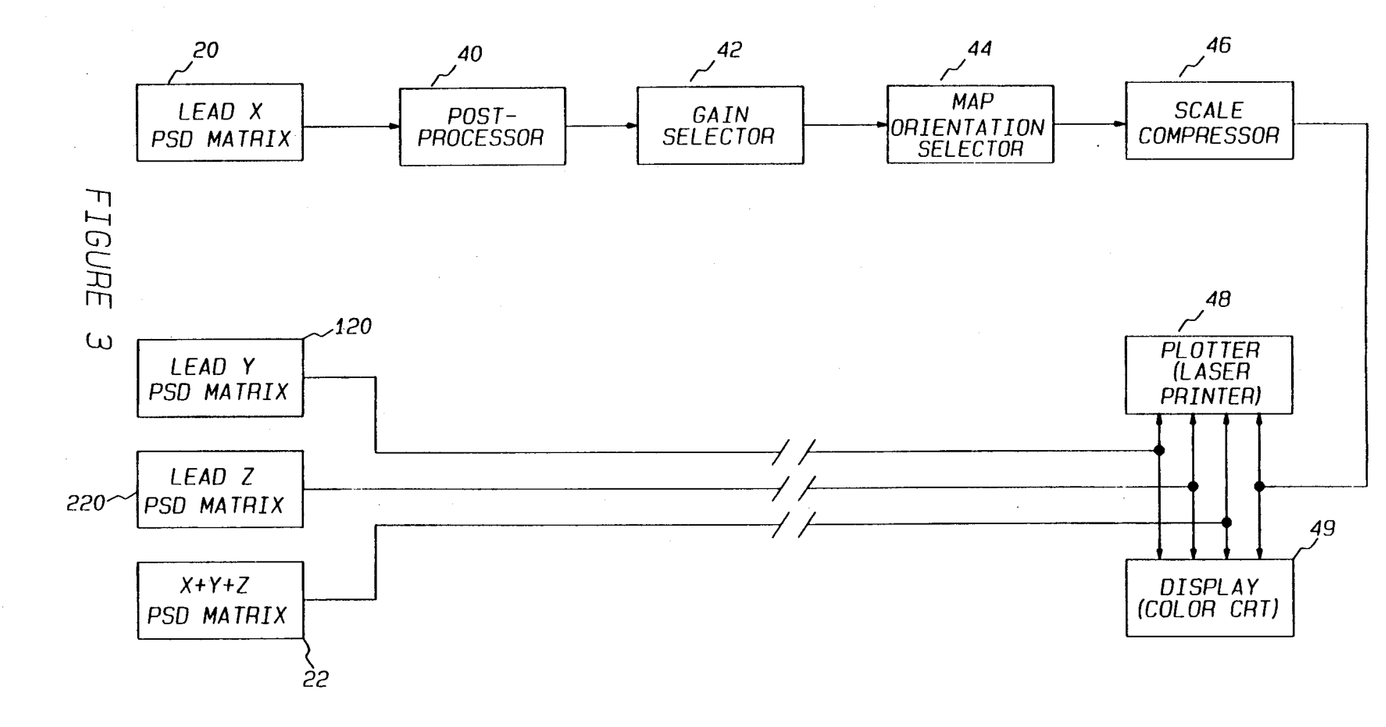
FIG. 3 is a block diagram of a means of the preferred embodiment for displaying and plotting spectral analysis data of the PSD matrices.
Figure 4A:
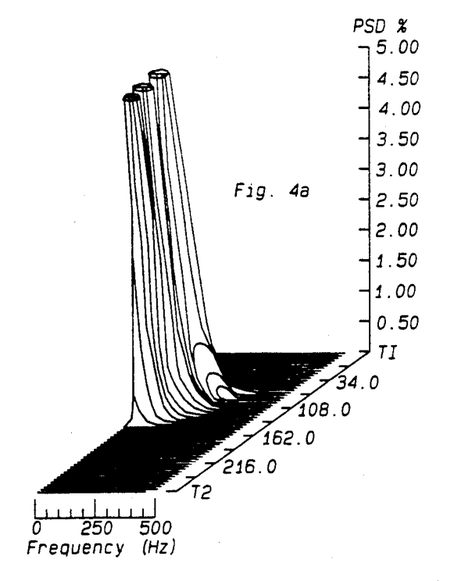
FIGS. 4a to 4f depict time domain plots and three dimensional Fourier spectral maps of the signal averaged electrocardiogram of a normal subject.
Figure 4B:
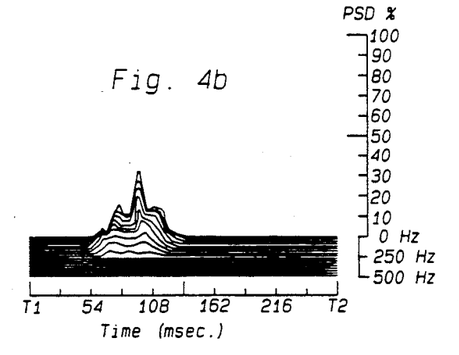
Figure 4C:
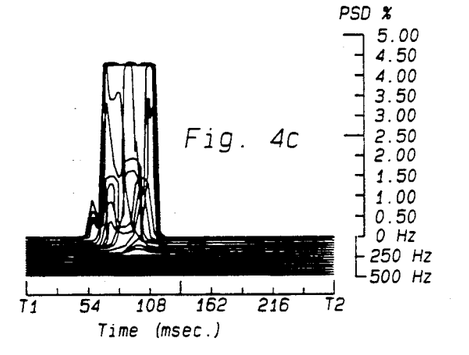
Figure 4D:
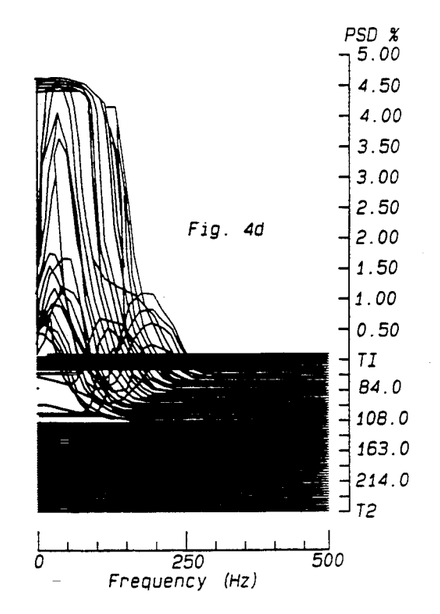
Figure 4E:
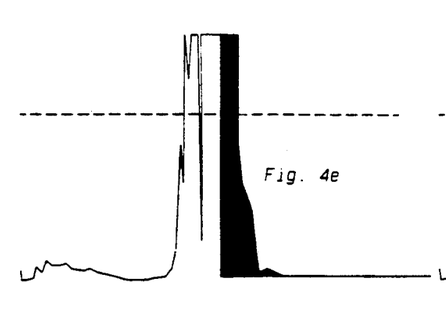
Figure 4F:
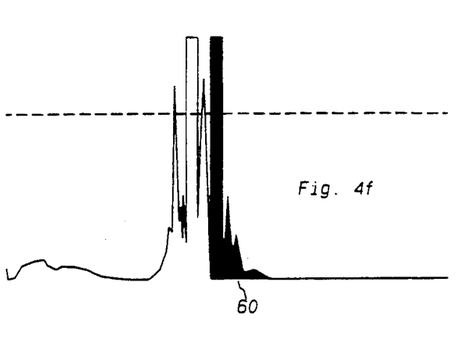
Figure 5A:
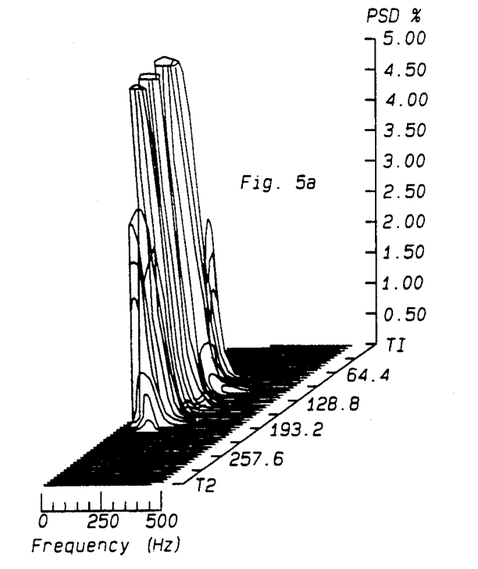
FIGS. 5a to 5f depict time domain plots and three dimensional Fourier spectral maps of the signal averaged electrocardiogram from a patient with late potentials and inducible SMVT.
Figure 5B:
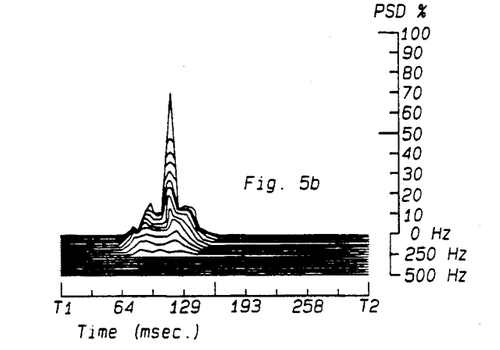
Figure 5C:
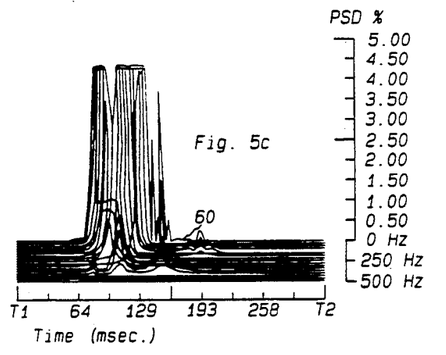
Figure 5D:
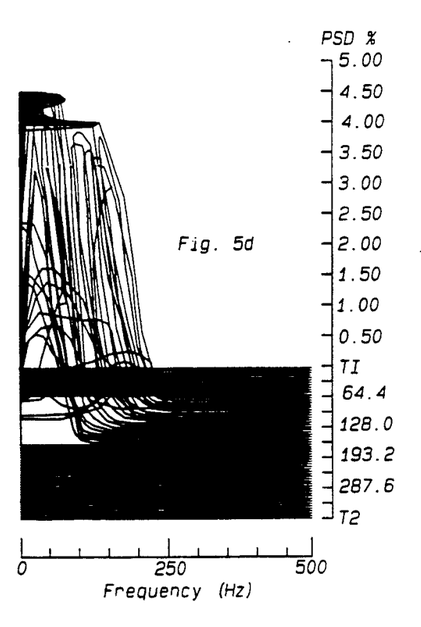
Figure 5E:
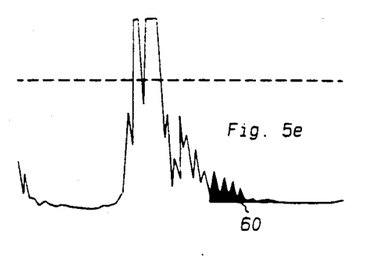
Figure 5F:
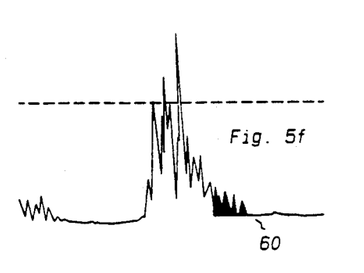
Figure 6A:
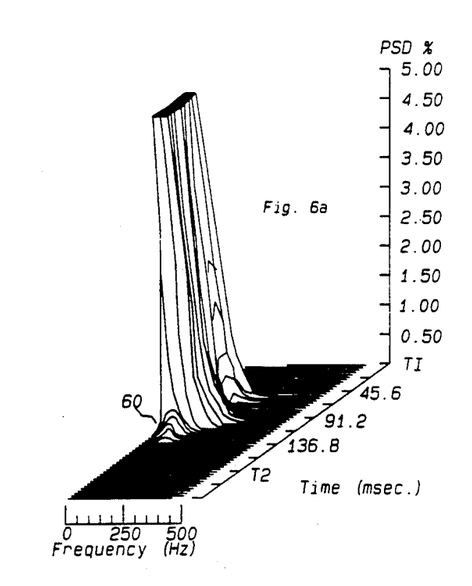
FIGS. 6a to 6f depict time domain plots and three dimensional Fourier spectral maps of the signal averaged electrocardiograms of a false-positive patient in whom late potentials are present but SMVT is not inducible.
Figure 6B:
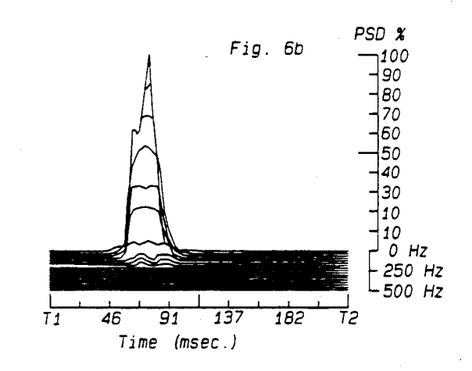
Figure 6C:
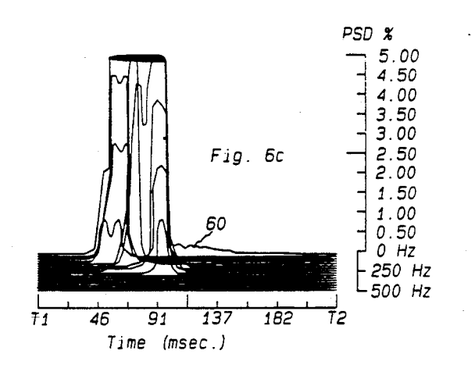
Figure 6D:
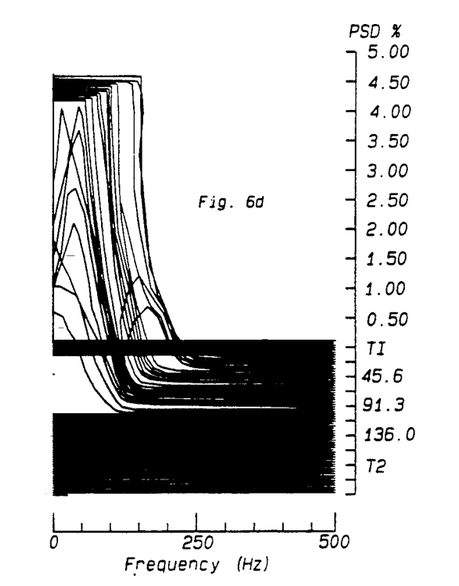
Figure 6E:
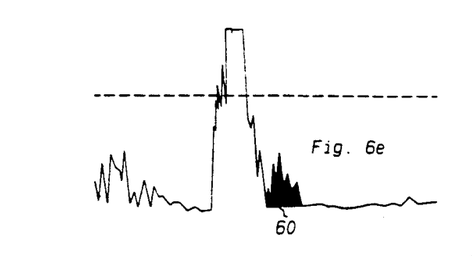
Figure 6F:
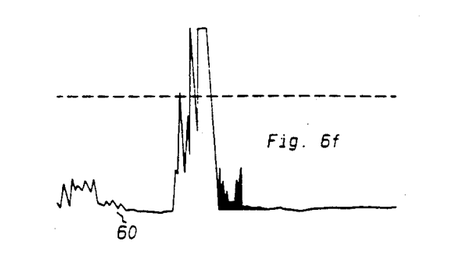
Figure 7A:
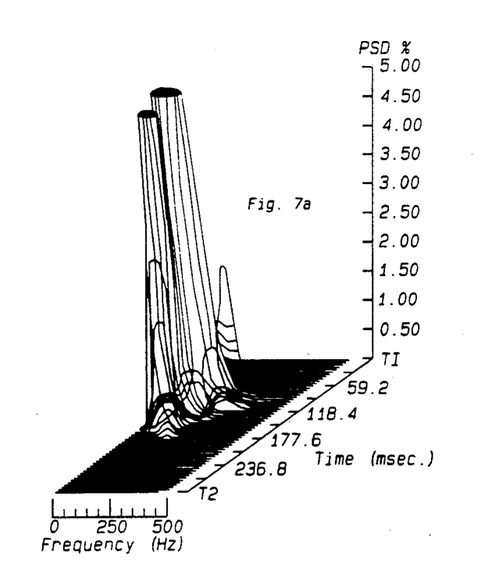
FIGS. 7a to 7f depict time domain plots and three dimensional Fourier spectral maps of the signal averaged electrocardiogram of a false-negative patient in whom late potentials are absent but SMVT is nevertheless inducible.
Figure 7B:
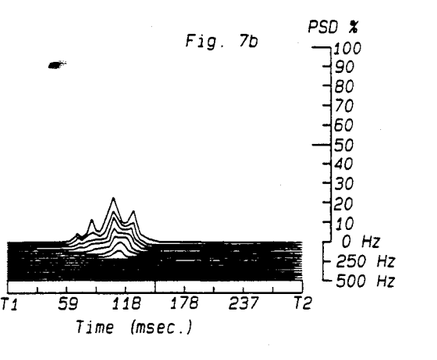
Figure 7C:
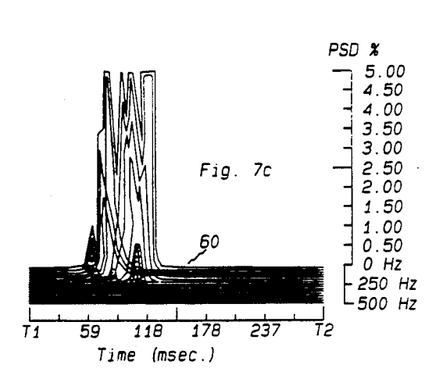
Figure 7D:
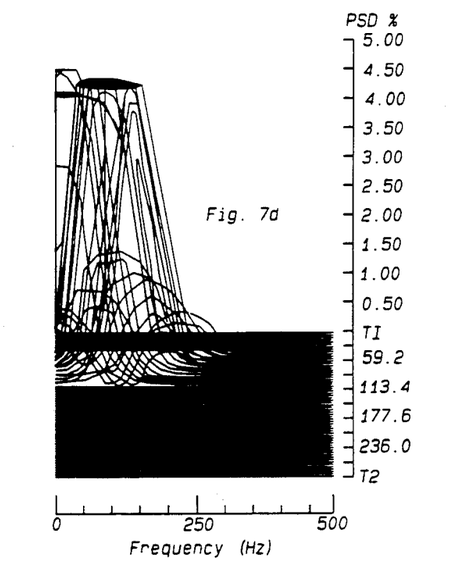
Figure 7E:
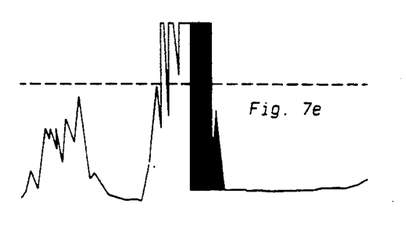
Figure 7F:
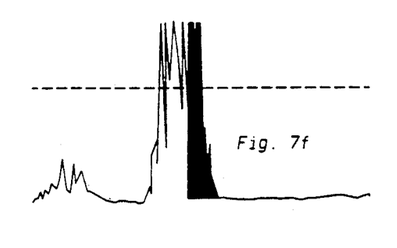

FIGS. 1, 2 and 3 are block diagrams of a basic embodiment of an apparatus for the spectral analysis of electrocardiographic signals according to the present invention. Much of the apparatus OF FIGS. 1, 2 and 3 can be implemented as software modules running on a microprocessor system. A simplified block diagram of the ECG frequency analysis system according to the present invention is shown in FIGS. 1, 2 and 3. As shown, most of the processing is performed separately but in identical fashion upon each of three X, Y and Z channels of the surface electrocardiogram. For simplicity, only the processing carried out on channel X is shown in detail, except where there is a combination of data from more than one channel.

As shown in FIG. 1, three orthogonal X, Y and Z channels 10, 110 and 210, respectively, of bipolar electrocardiographic signal are acquired over a time span of several hundred beats, either in real time by attachment of an appropriate isolated preamplifier directly to the patient, or from some other source, such as a previously recorded twenty-four hour Holter magnetic tape played back through an appropriate scanning device.

The actual signal processing commences by analog to digital conversion 11, of the three channels of ECG signal which are digitized at greater than five-hundred samples per second and typically at one-thousand samples per second, with resolution of at least one-point-five micro-volt per bit stored in computer memory or on some permanent storage medium, not shown.

Signal averaging 12 is performed in order to reduce background noise to a level generally considered acceptable for conventional time domain late potential analysis. Background noise is preferably less than one micro volt RMS from twenty-five to two-hundred and fifty Hertz. Generally, some two-hundred to five-hundred heart beats are needed to be averaged to achieve the desired noise reduction. After signal averaging 12 is computed, the average signal is stored on magnetic disk, not shown, for subsequent processing and analysis.

In order to provide both a routine clinical tool and a flexible research tool, analysis can be performed in either of two modes which are the automatic default mode and the manual mode. The signal processing performed in automatic default mode, whereby spectral turbulence over the whole QRS complex is computed by four separate statistical parameters which are ultimately combined to yield a single diagnostic spectral turbulence score is at the heart of this invention, and has been shown in a large clinical study to have greater predictive accuracy for SMVT than any non-invasive technique of the prior art. However, spectral turbulence analysis may be performed on user selected portions of signal or may include additional or different statistical measures of turbulence. The preferred embodiment therefore allows the user to optionally vary certain analysis parameters for research purposes. These user options are available in manual mode and are included in the following description.

In automatic default mode, the analysis is carried out upon issue of a single keystroke command, according to a predefined set of processing parameters and culminates in the printing of spectral maps and a numeric printed report. Otherwise, the user may access a menu prior to initiating the analysis, from which alternative analysis parameters in a wide range may be selected.

Referring still to FIG. 1, the region of ECG signal over which the subsequent analysis is to be performed is selected 13. In default mode, the QRS region is located by a computer algorithm, and many suitable algorithms are known to those skilled in the art. The whole of the QRS region is selected 13 for spectral analysis in the preferred form. The QRS signal region commencing twenty-five milli seconds before and terminating one-hundred-and-twenty-five milli seconds after the QRS complex is demarcated. In manual mode, the user indicates by using a mouse operated cursor the onset, i.e.

the beginning, and offset, i.e. the end, of the region to be analyzed, as well as the orientation to be used for plotting of maps. Because of the three-dimensional nature of the frequency spectral plots as exemplified in FIGS. 4a-d, 5a-d, 6a-d and 7a-d, low amplitude waveforms of interest may be obscured behind larger ones. If interest is primarily in signals occurring before the QRS such as the P wave or HIS bundle, then the maps may be plotted with these structures in front so as not to be obscured by the much larger QRS waveform itself. On the other hand, if interest is primarily in signals such as late potentials which occur after the QRS as when in the default condition, then the maps are plotted in reverse direction, with later occurring structures plotted in front of the earlier occurring QRS.

The next step in analysis is signal preprocessing 14. In the default mode, the first derivative of the signal-averaged ECG is calculated for each segment according to the following formula:

$$y[t] = (x[t+1] - x[t-1])/2 + (x[t+2] - x[t-2])/8$$

where y[t] is the wave front velocity, i.e. amplitude derivative, of the signal at sampling time t, and where x[t+1], x[t-1], x[t+2] and x[t-2] are the amplitudes of the adjacent sampled time points. In manual mode, the user may elect, to substitute for the first derivative function of the preprocessing step 14 either no signal modification whatsoever or the second derivative calculated according to the formula:

$$y[t] = x[t+1] + x[t-1] - 2(x[t])$$

using the same nomenclature as for the first derivative equation above. The undifferentiated ECG signal represents amplitude of the depolarization wavefront as a function of time. The first derivative corresponds to velocity, while the second derivative is analogous to wavefront acceleration. Use of the first derivative in default mode is preferred as it minimizes the undesirable effect whereby a normal but sloping ST segment containing very high energy low frequency signal components obscures the presence of low amplitude late potentials in the spectral plots. The first derivative also acts to isolate late potentials based upon spectrocardiographic features, if desired. Although the spectral turbulence measurements of the present invention provide superior predictive accuracy and in a sense therefore supersede late potential analysis, the preferred embodiment does provide for the identification and quantification of late potentials should they be present.

Preprocessing 14 includes a selection of either the first or second derivative so as to eliminate high energy low frequency signals which may obscure low amplitude late potentials. The first and second derivative have been shown to work well for isolating spectral turbulence as well as for removing any slope of the base line. The derivative function also affects the frequency spectra of the finished plotted maps, in a beneficial way. The primary information sought is the relative changes in the velocity of the QRS wavefront as it propagates through the heart tissue. Changes in the velocity of the wavefront result as the wavefront winds around non-uniformly functioning heart cells. The wavefront is thus a vector experiencing radical velocity changes, including speed, amplitude and direction during its propagation through non- uniformly conducting heart tissue. The first derivative and second derivatives, and preferably the first derivative are particularly suitable for isolating changes in the velocity of the wavefront. The first derivative acts to shift the harmonics, i.e. the frequency components of the Fourier spectrum, towards the higher harmonic frequencies so as to emphasize them at the expense of the lower harmonic frequencies. This shift acts to improve the effective frequency resolution of subsequent processing steps so as to allow meaningful determinations of frequency spectral content of signal segments of shorter duration than would be possible without derivative preprocessing.

The time span of the signal region of interest is divided by a signal segmentor 15 into overlapping time segments of equal length according to the region selection 13. In the default mode, time segments are of twenty-four milli seconds in duration and each successive segment commences two milli seconds later than its immediate predecessor. For example, if the signal region to be analyzed is two-hundred and forty milli seconds long, then there would be 1+(240−24)/2 segments, or one-hundred and nine segments submitted to further processing in the preferred form. In manual mode, segment length may be specified in a range from five milli seconds to one-hundred and fifty milli seconds, while step interval may be specified in a range from one to twenty milli seconds. For predicting those at risk from SMV·T, the whole of the QRS is selected in the preferred form, even though spectral turbulence may be analyzed respecting any portion of the QRS complex.

Each time segment is then successively processed through a mean substractor 16, windower 17, FFT 18 and PSD calculator 19, until a two dimensional PSD matrix table 20 is built in computer memory. Each PSD matrix table has a row for each time segment and a column for each frequency component of the FFT 18. The PSD table 20 contains the power spectral densities for each FFT frequency component for each time segment over the region of interest.

A normal QRS complex is less than one-hundred-and-twenty milli seconds in duration, whilst in abnormals it may approach two hundred milli seconds. The QRS region of interest is divided into time segments each of which is comprised of data points. In default mode, each time segment has twenty-five data points spanning twenty four milli seconds. Each data point has a respective amplitude value. The "mean value" of the signal for a time segment is the average amplitude of the data points in that time segment. In default mode, the mean value of the signal within a time segment is calculated for each time segment and subtracted by the mean substractor 16 from each data point within that time segment so as to remove any DC offset form the respective time segment. In manual mode, mean subtraction 16 may be overridden altogether or delayed until after window processing 17.

The windower 17 functions to multiply the data points of each time segment by a suitable weighting function in order to minimize spectral leakage and effects of edge discontinuities inherent in the Fast Fourier Transformation 18. In the default mode, each time segment is multiplied by a four-term Blackman-Harris window function of equal length, but other Rectangular, Hanning or Hamming window options may be substituted in manual mode. The application of a suitable window permits the valid application of an FFT to a signal of relatively short duration, and is a standard procedure familiar to those skilled in the art.

In manual mode, windowing may be followed by mean subtraction 16 to remove DC offset but in the default mode mean subtraction 16 is executed prior to windowing 17.

The processing step 18 is performance of a discrete Fast Fourier Transform (FFT) on each time segment. The time segment data point values are first moved to the beginning of a memory array, the end of which is then padded with zeros to fill the entire length of the desired FFT. In default mode, a sixty-four point FFT is used but in manual mode a thirty-two to one-thousand and twenty-four data point FFT may be selected instead. For a default time segment length of twenty-four milli seconds represented by twenty-five data points and a sixty-four point FFT, points twenty-six to sixty-four are set to zero after which a double precision discrete FFT 18 is executed. The number of FFT points must be at least equal to the number of data points per time segment. Increasing the number of FFT points beyond the number required to hold all the points in a time segment increases the visual smoothness of the three dimensional maps, but does not increase the resolution or accuracy of any statistical calculations.

The time-domain waveform for each time segment is thus separately transformed by the FFT 18 to a corresponding series of Fourier frequency components.

Power Spectral Density Calculator 19 computes the power spectral density (PSD) for each Fourier frequency component by summing the squares of the imaginary and real Fourier coefficients. The PSD values are computed, collected and stored into successive rows of the PSD matrix table 20 for each successive time segment. A PSD matrix, i.e. power density matrix of time segment rows and frequency component columns, for each lead forms the matrix tables 20, 120 and 220 for each lead X 10, lead Y 110, and lead Z 210, respectively.

The processing of Lead X by steps 10 though 20, is identical to the processing of Lead Y steps 110 to 120, and Lead Z steps 210 to 220. The processing for each time segment within each X, Y and Z ECG leads 10, 110 and 210, respectively is used to build the X, Y and Z PSD matrix tables 20, 120 and 220, respectively, spanning the whole of the ECG signal region of interest. These PSD tables 20, 120 and 220 are then used to generate spectral maps or to calculate further numeric parameters.

Referring to FIG. 2, the X, Y and Z PSD matrices, 20, 120 and 220, are used to produce the X+Y+Z PSD matrix. This fourth X+Y+Z PSD matrix 22 contains the mean values of the X, Y and Z PSD matrices 20, 120 and 220. The X+Y+Z PSD Matrix 22 is thereafter displayed, plotted and quantified identically to the displaying, plotting and quantifying processing applied to each of the X, Y and Z PSD matrices 20, 120 and 220, as shown in FIGS. 2 and 3. Although the X+Y+Z PSD Matrix 22 is not used for calculation of spectral turbulence in the standard default mode of operation, it is available for use in manual mode.

From the visual plots depicted in FIGS. 4a-d, 5a-d, 6a-d and 7a-d and from experimental data it has been discovered that the spectral maps of abnormal patients are conspicuously more "turbulent", with spectral contours less smooth than those of normal persons. For example, a comparison of the spectral plots of FIGS. 4a-d and 6a-d, vis-a-vis the respective spectral plots of FIGS. 5a-d and 7a-d, shows that the patients of FIGS. 4a-d and 6a-d have less spectral turbulence and smoother looking spectral plots than do the patients of FIGS. 5a-d and 7a-d. Numeric calculations represented in FIG. 2 quantify many of the differences between normal and abnormal spectral contour maps so as to allow development of precise classification criteria. Each calculated parameter corresponds to a qualitative visual difference apparent from comparison of normal and abnormal spectral maps.

Referring to FIG. 2, each row of the PSD matrices 20, 120, 220 and 22 contain the PSD values for each Fourier frequency component of a single time segment. The Fourier frequency components of each time segment include a fundamental and harmonic frequency components of the same frequencies but having differing Fourier coefficients and respective PSD values. An additional column which is referred to as the total PSD column computed by summer 23 is added to the matrix table for each ECG lead by summing the PSD value for all of the frequency components for each row i.e. time segment, to represent the sum total power spectral density for each time segment. At the fiducial segment locator 24, a central reference time segment of the QRS complex is identified. The fiducial time segment is that row with the highest total PSD in the total PSD column computed by summer 23. The fiducial time segment is thus the time segment in the PSD matrix 20, 120, 220 or 22 of the highest total power.

The mean background noise value and standard deviation are calculated by calculator 25 by identifying that forty milli second region, i.e. twenty-one consecutive time segments at the default step interval of two milli seconds in the preferred form, within the total PSD column having the lowest average total PSD. Signal averaging 12 of FIGURE 1 reduced background noise but did not eliminate it completely. The mean background noise value is based upon a forty milli second region of lowest total power and is thus defined as noise. The mean and standard deviation of that noise is calculated by calculator 25 based upon the signal of this region.

The time segment rows corresponding to QRS onset and offset are next located 26. The QRS complex region is variable from patient to patient and the locator 26 is the means for identifying the QRS complex. The QRS offset, that is end, is defined in the preferred form of the invention as that first row, i.e. the first time segment, found searching away from the QRS fiducial segment 24 and searching towards the end of the QRS complex, and having total PSD value less than five standard deviations above the mean background noise level found by the noise calculator 25. Thus, QRS offset is deemed to occur when the total power at all frequencies has fallen to below five standard deviations above mean noise level. QRS onset, i.e. the beginning of the QRS complex, is defined as the first row moving from the fiducial point towards the beginning of the QRS complex whose total PSD value falls below point-two percent of that of the row identified as the fiducial point found by locator 24. Thus, the QRS onset is determined by searching from the fiducial point towards the beginning of the QRS signal to the two percent point, whereas the offset is determined by searching from the fiducial point towards the end of the QRS complex until the signal falls below five standard deviations above the mean background noise. QRS onset based upon a two percent of the fiducial value and offset based upon five standard deviations above the mean noise in the preferred form are only examples and other definitions of identification of the QRS onset and offset are also suitable.

The sum of the total PSD over the terminal forty milli seconds of the QRS complex, demarcated by locator 26, is computed by calculator 27 as the PSD40 value. It has been discovered according to the present invention that the value of this PSD40 parameter, is higher in normal patients than in those with time domain late potentials. PSD40 computation by calculator 27 is the sum of the power over the QRS last terminal forty milli second region of the QRS complex ending at the QRS offset. The PSD40 forty milli second region is analogous to the RMS40 region the prior art. Although not used to estimate spectral turbulence, it is provided in manual mode for research purposes in the preferred embodiment.

From the total PSD column calculated by summer 23, a low power region is located and defined by locator 28 as that region commencing at the first time segment following the fiducial QRS segment having total PSD less than point-two percent of the fiducial segment, and terminating at the QRS offset. This low power region is analogous to the late potential region of conventional time domain analysis. Thus, the low power region is used to locate the probable approximate region of the late potential region, and is defined as the region from the first time segment after the fiducial QRS having and having less than point- two percent of the PSD of the fiducial segment, to the end of the QRS complex. The high power region is located by locator 29 as that region between the QRS onset and the Fidicual point identified by locator 24. Thus, the total QRS complex demarcated at locator 26 is divided into a low power region and a high power region, by locators 28 and 29, respectively. Although not used for spectral turbulence analysis in automatic default operating mode, demarcation of a late potential zone from the rest of the QRS is provided by the preferred embodiment, in manual mode only, to facilitate late potential frequency analysis for research purposes.

A further set of numerical computations is executed separately upon the low power and total QRS regions defined by locators 28 and 29, although only those performed upon the whole region are used for SMVT prediction in default automatic mode. For brevity, the distinction between the low power region and the high power region, or any other predefined identified region, is not significant because the processing performed upon any region over the whole QRS region is identical, in the preferred form of the invention.

One of the possible differences between spectral maps from normal and abnormal patients is a difference in the number of spectral peaks evident on the spectral maps, especially at higher frequencies. Accordingly, a peak counter 30 makes counts of spectral peaks within a region, e.g. the low power terminal QRS region, by six separate criteria. First, peaks are classified according to whether they occur above or below two-hundred and fifty Hertz i.e. high frequency peaks or low frequency peaks. Then, separately for both high and low frequency peaks, peak counts are made of peaks occurring in the frequency axis along rows of the PSD matrix tables i.e. frequency axis peaks, in the time axis along columns of the PSD table, i.e. temporal axis peaks, or in both axes simultaneously, i.e. biaxial peaks. Thus, the peak counter 30 uses six separate criteria: peaks along frequency axis for harmonic frequencies greater than two-hundred and fifty Hertz; peaks along frequency axis for harmonic frequencies less than two-hundred and fifty Hertz; peaks along the time axis for harmonic frequencies greater than two-hundred and fifty Hertz; peaks along the time axis for harmonic frequencies less than two-hundred and fifty Hertz; peaks along both axis for harmonic frequencies greater than two- hundred and fifty Hertz; and peaks along both axis for harmonic frequencies less than two-hundred and fifty Hertz. Patients who have time domain late potentials and ventricular arrhythmias may also have higher peak counts than do patients with late potentials but with no proneness to SMVT. A characteristic of abnormal patients include high peak counts in the main high power QRS region as well as in the late potential region. A peak is defined as a point having a value which is greater than a predecessor and successor value, in the preferred form, or may be defined as a value which is greater than a predecessor and the two successor values, or some other suitable method. So far however, peak counts have not been found to be among the best determinative indicators for those patients prone to SMVT, and therefore are not part of the automatic default analysis protocol, even though they are provided in manual mode.

A second additional column is calculated by an intersegment correlation calculator 31 for each PSD matrix table 20, 120, 220 and 22, containing the Pearson correlation coefficient of each row with the row immediately below it, in the preferred form. This new column generated by the intersegment correlation calculator 31 represents the degree to which the frequency spectrum of each time segment resembles the frequency spectrum of the adjacent time segment. This column of intersegment correlation coefficients is next used to yield several further significant numeric statistical parameters of spectral turbulence.

Calculator 31 calculates an the Intersegment correlation which is the degree to which one time segment's frequency components correlates with its neighbor, that is the correlation of the coefficients of the Fourier frequency components of one time segment to its neighbor. An intersegment correlation for each time segment over the QRS region of interest is calculated by calculator 31. The intersegment correlations are stored respecting each row, that is time segment for each of the matrices 20, 120, 220 and 22. The Pearson method is a well known standard method for generating correlation coefficients between two set of numbers. A correlation coefficient value of numeric one indicates identical frequency makeup of two adjacent time segments.

The number of instances of a low intersegment correlation coefficient having a value less than a predetermined threshold value, e.g. 0.985, is counted by counter 32. The threshold value used in the preferred embodiment is by way of example only, having been arrived at empirically during a clinical validation study, which demonstrated that normal subjects had fewer instances of poor interslice correlations than did abnormal patients prone to SMVT. Low intersegment correlation counter counts the number of segments with poor correlation, i.e. number intersegment correlation having a correlation of less than a predefined value.

A calculator 33 performs intersegment correlation mean and intersegment correlation standard deviation of the intersegment correlation coefficients of the column calculated by calculator 31. It has been discovered that the time segments of normal patients have a higher mean correlation and lower standard deviation than abnormal patients. Significantly, it has been discovered that the intersegment correlation mean value is the best single determinative indicator of patients prone to SMVT. The intersegment correlation mean value is the best single indicator of overall spectral turbulence throughout the whole QRS complex. When the wave front either significantly slows down or winds around a corner of suspect heart tissue resulting in substantial velocity vector changes of the depolarization wavefront, there will be a relative change of the coefficients of the harmonics for the corresponding time segment. Because the frequency domain is used, the substantial velocity vector changes will produce a relative change in the coefficients of the harmonics. Uniform heart muscle should produce a relatively constant and high intersegment correlation. Uniform heart muscle should produce high mean intersegment correlation coefficient with a relatively low standard deviation. The intersegment correlation mean and standard deviation are thus indications of general spectral turbulence and general non-uniformity of conduction in heart tissue reflected by corresponding wave front velocity changes. A relative change in the coefficients of the harmonics for the time segment will cause a relative change to the mean correlation. Non-uniformly conducting heart muscle thus produces a greater variation of intersegment correlations having a lower mean and a greater standard deviation.

Calculator 34 computes an intersegment correlation ratio. The intersegment correlation ratio is calculated by dividing the low correlation count 32 by the number of segment pairs evaluated. Thus, the intersegment correlation ratio is found by dividing the number of instances of a correlation coefficient less than a predetermined value by the number of intersegment pairs, so that it represents the proportion (rather than the absolute number) of all interslice correlations that fall below a threshold value.

The calculator 35 calculates another spectral turbulence statistical parameter called spectral entropy. Spectral entropy represents the degree to which the frequency spectra of time segments differ from the average frequency spectrum of the region as a whole. Spectral entropy is calculated by calculator 35 based from a correlation of each time segment to an average PSD row having the same set of Fourier frequency components. Thus, an additional row is created and added to the PSD matrix table into which is stored the average PSD for each respective set of frequency components including the fundamental and harmonics frequency components. The average PSD Nth harmonic is equal to average of all of the Nth harmonics of all the rows. Each and every time segment row is correlated to this new row of average PSDs. The average of the correlation is next calculated and then subtracted from 1 to yield the spectral entropy statistical parameter for the region of interest. Thus, spectral entropy, that is, spectral disorganization, is equal to one minus the average PSD correlation coefficient for all the segments correlated to the mean PSD. The average PSD for each frequency component over a region of interest is thus first computed followed by a Pearson correlation between this ideal average PSD row and each of the time segments. The resulting correlation coefficients are then averaged and subtracted from one to indicate entropy disorganization. It has been found according to the discoveries of the present invention that normal patients have lower spectral entropy values than abnormal patients.

Data Registers 36, 136, 236 and 336 store all of the statistical parameters and numeric data derived from the PSD matrices 20, 120, 220 and 22, respectively, and are available for printing by report generator 38. The statistical parameters and numeric data derived from the PSD matrix 120, 220 and 22 is calculated identically to the lead X PSD matrix 20. The set of statistical parameters are collected and combined together by generator 38 with identically calculated statistical parameters leads Y, Z and the average $X+Y+Z$ PSD matrix to form data for printed report in various printed formats. Generator 38 also performs the calculation of a single number, referred to as Spectral Abnormality Score, useful for clinical diagnosis, as follows. For each lead X, Y and Z and each statistical spectral turbulence parameter Low Slice Correlations Ratio, Inter-slice Correlation Mean, Inter-slice Correlation Standard Deviation, and Spectral Entropy, the result is compared with a normal threshold value. The cutoffs were obtained from a large clinical study performed by the inventor and further described towards the end of this section. In addition, the result for each spectral turbulence parameter is averaged over the three leads, and compared with a normal average value. For each abnormal average value a score of 1 is awarded and added to the previous score, such that zero is the most normal and four the most abnormal attainable score. In the preferred embodiment, this scoring system is applied to only the averaged spectral turbulence statistics over the three X, Y and Z leads because this was shown by clinical study to be the most accurate predictor of SMVT vulnerability. However, almost as good results are obtainable by scoring each lead individually.

Referring to FIG. 3, representing the PSD matrices 20, 120, 220 and 22 also used to generate visual CRT displays and the plotted spectral contour maps exemplified in FIGURES 4a-d, 5a-d, 6a-d and 7a-d. In manual mode, the user may optionally elect post-processing to display or plot not the values actually contained in the PSD matrix tables but rather their first or second derivatives with respect to time. In the default mode no calculations or changes are made. If the first derivative post-processing which corresponds to velocity, is selected at each time segment row is subtracted from the row above it thus representing the change in PSD at each segment step. If second derivative post-processing, which corresponds to acceleration is selected, then each time segment row is subtracted from the mean of the row immediately above and the row immediately below it. This optional post-processing 40 may accentuate some of the visual differences between the maps of normals and abnormal patients.

The display and plotting gain is determined by the gain selector 42. The gain selector 42 is set to twenty in the default mode, such that full scale corresponds to five percent peak PSD. The gain value of twenty is preferred and was found by experimentation to yield good resolution of the visual features useful in clinical diagnosis. In manual mode the user may select gains from point-zero-one to one-thousand.

The orientation of spectral maps to be plotted or displayed is selected by the map orientation selector 44. FIGS. 4a-d, 5a-d, 6a-d and 7a-d depict various views of the three dimensional graphs from various perspectives. No single view is perfect for observing all features of potential interest. In the default mode, all available views are automatically plotted or displayed. In the manual mode, the operator may select a single view or any combinations of views.

In addition to gain and view selection by selectors 42 and 44, the invention provides for optional non-linear scale compression by scale compressor 46 in the manual mode prior to displaying by CRT 49 or plotting by plotter 48. In the default mode, PSD values are used. In manual mode the user may select Power, i.e. square root of PSD, or logarithmic decibel (Db) i.e. −20log(PSD), representation of the spectral power densities instead.

Referring now to FIGS. 5a-f and 6a-f, some examples of the benefits of the invention are shown by recordings made from exemplar patients. FIGS. 5a-f are from a patient who has suffered a heart attack and has had multiple episodes of life threatening arrhythmia. FIGS. 6a-f is from a normal healthy patient with no heart disease and no proneness to ventricular arrhythmia. Although not at risk, the patient of FIGS. 6a-f has a common minor normal variant of the electrocardiogram known as incomplete right bundle branch block which results in the end portion of the QRS complex being slightly slurred. Such slurring results in a false-positive late potential 60, and the patient of FIGS. 6a-f might be incorrectly classified, according to the teaching of the prior art, as at risk on the basis of a test for presence of late potentials. The late potential signals 60 are indicated on both FIGS. 5a-f and 6a-f. Both patients have late potentials 60 extending out beyond the end of the QRS complex. However, in FIGS. 6a-f the spectral contours of the spectral plots of the false-positive patient are smooth, whereas in FIGS. 5a-f the true-positive spectral contours are turbulent and disorganized. There is much more turbulence of spectral contours appearing throughout the whole QRS complex of the true-positive patient of FIGS. 5a-f and not just at the late potential region. The patient of FIGS. 6a-f has smooth spectral contours despite the presence of late potentials. The above examples illustrate one instance of how the present invention provides a means for determining the correct risk classification of a patient who would be misdiagnosed as at risk by techniques of the prior art which was based primarily on the presence of late potentials.

In a recent clinical study submitted for publication in the medical literature, the inventor investigated the predictive accuracy of the spectral turbulence scoring system comprehended above, comparing it to the predictive accuracy for inducible SMVT of conventional time domain late potential analysis of the prior art. One hundred and forty two subjects were studied, divided into four groups. Of seventy-one clinically normal patients without time domain late potentials, one-hundred percent had spectral turbulence 4 scores of two or less. Of thirty-two patients with both time domain late potentials and inducible SMVT, thirty-one had spectral abnormality scores of three or four, while only one had a score of two. Of twenty-eight patients classified late potential positive by time domain analysis in whom there was no evidence of SMVT by either clinical history, i.e. normal patient, or at electrophysiologic study, time domain false-positive patients, twenty-four patients or eighty-six percent had spectral turbulence scores of two or less indicating normality, whilst four patients, that is fourteen percent, had abnormal scores of three or four. Often patients with inducible SMVT at electrophysiologic study in whom time domain analysis was negative for late potentials, six, this is sixty percent, had abnormal spectral turbulence scores of three or four whilst four patients, that is forty percent, had normal scores of two or less. Combining the results of the last two groups, spectral analysis correctly classified thirty of the thirty-eight patients, that is seventy-nine percent, who were incorrectly classified by time domain late potential analysis. Total predictive accuracy of frequency analysis for all groups was ninety-four percent, as compared with seventy-three percent for time domain late potential analysis. The positive predictive accuracy was ninety percent and the negative predictive accuracy was ninety-five percent of the present invention as compared to fifty-four percent and eighty-eight percent, respectively, for time domain analysis. The sensitivity was eighty-eight and the specificity was ninety-six percent for the present invention as compared to seventy-seven percent and seventy-two percent, respectively, for time domain analysis. The overall predictive accuracy of spectral turbulence analysis has thus been shown to be significantly greater than that of time domain late potential analysis.

The present invention teaches that myocardial regions with abnormal conduction characteristics can result in a quantifiable degree of spectral turbulence, that is, the : nature and extent of these conduction abnormalities both anatomically and electrophysiologically. The present inventor has discovered a relationship between the spontaneous and/or inducible reentrant tachyarrhythmias and the quantifiable degree of spectral turbulence. The present system and method involves the quantifying and scoring of spectral turbulence as an indication of patients at cardiac arrhythmia risk. Selection of the inducibility of SMVT at electrophysiologic study as the standard against which the spectral technique is supported on electrophysiologic grounds.

The invention disclosed herein is capable of achieving objects and advantages over the prior art. The preferred description of the preferred embodiment is illustrative of an example of methods and apparatus of the invention. Those skilled in the art will recognize that the apparatus may be implemented with alternate means, and method of differing process steps may perform the substantially the same functions described above. Those skilled in the art may make modifications, equivalents, and adaptations to the preferred embodiment of the present invention, but such modifications, equivalents and adaptations may nonetheless fall within the scope of the invention as particularly pointed out by the appended claims.

What is claimed is:

1. A method for detecting abnormalities of heart having a time varying QRS signal, said method comprising the steps of
    partitioning said QRS signal into a sequence of time displaced time segments,
    transforming said time segments into respective sets of spectral components, and
    correlating said sets of spectral components across the QRS signal, and
    generating an abnormality score when the correlation of said correlating step is above a predetermined state.

2. The method of claim 1 wherein said transforming step comprises the step of
    partitioning each of said time segment into data points, and
    executing a Fourier Transform upon the data points.

3. The method of claim 1 wherein said transforming step comprises the step of
 filtering said QRS signal into spectral components, and
 isolating said spectral components by time segment.

4. The method of claim 1 further comprising the step of signal averaging said QRS signal prior to said partitioning step.

5. The method of claim 1 further comprising the step of generating spectral turbulence parameters based upon the degree of correlation of said sets of spectral components.

6. The method of claim 1 further comprising the step of differentiating said QRS signal prior to said transforming step.

7. The method of claim 1 wherein said correlating step comprising the steps of
 correlating successive pairs of sets of spectral components of respective successive time segment pairs,
 generating an intersegment correlation mean, and
 assigning an abnormality value when said intersegment correlation mean is above a predetermined value.

8. The method of claim 1 wherein said correlating step comprising the steps of
 correlating successive pairs of sets of spectral components of respective successive time segment pairs,
 generating an intersegment standard deviation, and
 assigning an abnormality value when said intersegment correlation standard deviation is above a predetermined value.

9. The method of claim 1 wherein said correlating step comprising the steps of
 correlating successive pairs of sets of spectral components of respective successive time segment pairs,
 generating an intersegment correlation ratio based upon the percentage of intersegment correlations is below another predetermined value, and
 assigning an abnormality value when said intersegment correlation mean is above a predetermined value.

10. The method of claim 1 wherein said correlating step comprising the steps of
 computing an average set of spectral components,
 correlating each of said sets of spectral components of said respective time segments to said average set of spectral components,
 generating a spectral entropy value based upon said correlation of said average set of spectral components, and
 assigning an abnormality value when said spectral entropy is above a predetermined value.

11. The method of claim 1 wherein said generating step comprises the step of,
 computing an abnormality score based upon equal weight of intersegment correlation mean, intersegment correlation standard deviation, intersegment correlation ratio, and spectral entropy spectral turbulence correlations over the QRS region, and
 displaying said abnormality score.

12. A method for detecting abnormalities of heart having a time varying QRS signal, said method comprising the steps of
 signal averaging an ECG signal
 identifying the QRS signal of said ECG signal,
 differentiating said QRS signal
 dividing said differentiated QRS signal into a sequence of overlapping time segments,
 dividing each of said time segment into data points,
 multiplying data points of each of said time segments by a window function to weight each time segment,
 performing a discrete fast Fourier transform on each said windowed time segments, in which the power spectral density of a series of frequency components are calculated, and
 producing a numerical matrix or table of power spectral densities are located by frequency components and time segments,
 correlating said power spectral densities of said frequency components with each other across the QRS signal,
 computing an spectral turbulence parameters based upon the correlation of said power spectral densities,
 assigning an abnormality state in the presence of abnormal spectral turbulence.

13. The method of claim 12 further including locating the onset and offset of the QRS portion of said ECG signal.

14. The method of claim 12 wherein said spectral turbulence parameters comprise intersegment correlation mean, intersegment correlation standard deviation, intersegment correlation ratio, and spectral entropy.

15. The method of claim 12 wherein said abnormality state is determined by an abnormality score above a predetermined value, said abnormality score incremented for each of said spectral turbulence parameters in an abnormal state.

16. The method of claim 12 wherein
 said time segments are between twelve and forty-eight milli seconds,
 said time segments are stepped between one and five milli seconds,
 said data points are one milli second apart, and
 said transform uses a matrix having points equals to at least the number of said data points of said time segment and equals a number of the power of two.

17. A method for detecting abnormalities of heart having a time varying QRS signal, said method comprising the steps of
 signal averaging an ECG signal
 identifying the QRS signal of said ECG signal,
 differentiating said QRS signal
 dividing said differentiated QRS signal into a sequence of overlapping time segments,
 multiplying each said time segment by a window function to weight each time segment,
 performing a discrete fast Fourier transform on each said windowed time segments, in which the power spectral density of a series of frequency components are calculated,
 producing a numerical matrix or table of power spectral densities are located by frequency components and time segments,
 correlating said power spectral densities of said frequency components with each other across the QRS signal,
 computing an spectral turbulence parameters based upon the correlation of said power spectral densities,
 assigning an abnormality state in the presence of abnormal spectral turbulence.

18. The method of claim 17 further including locating the onset and offset of the QRS portion of said ECG signal.

19. The method of claim 17 wherein said spectral turbulence parameters comprise intersegment correlation mean, intersegment correlation standard deviation, intersegment correlation ratio, and spectral entropy.

20. The method of claim 17 wherein said abnormality state is determined by an abnormality score above a predetermined value, said abnormality score incremented for each of said spectral turbulence parameters in an abnormal state.

21. The method of claim 20 wherein said computing step further comprises the step of
computing each of said spectral turbulence parameters for each of an X, Y and Z lead, and
averaging each of said spectral turbulence parameter on said computing Z, Y and Z lead whereby said abnormality score is incremented based upon an average of each of said spectral turbulence parameters in an abnormal state.

22. A system for detecting heart conditions comprising
first means for receiving said a QRS signal, and
second means for generating an abnormality indicator, said second means connected to said first means, for dividing said QRS signal into a sequence of overlapping time segments each have a plurality of data points, for transforming said data points of each of said time segments into a matrix ofpower content indicators organized by time segment and frequency components, for correlating said power content indicators of said frequency components with said correlation upon successive time segments, for generating at least one spectral turbulence parameter based upon the correlation of successive time segments with said abnormality indicator based upon the value of said at least one spectral turbulence parameter.

23. The system of claim 22 wherein said QRS signal is a time average QRS signal and wherein said second means identifies an onset and an offset of said QRS time averaged signal.

24. The system of claim 22 wherein said at least one spectral turbulence parameter is an intersegment correlation mean.

25. The system of claim 22 wherein said at least one spectral turbulence parameter is an intersegment correlation standard deviation.

26. The system of claim 22 wherein said at least one spectral turbulence parameter is an intersegment correlation ratio.

27. The system of claim 22 wherein said at least one spectral turbulence parameter is a spectral entropy value.

28. A system for detecting heart conditions comprising
first means for storing a sequence of QRS signals from a human heart,
second means for receiving said QRS signals form said first means,
third means for generating at least one abnormality indication, said third means connected to said second means, said third means for signal averaging said QRS signals, for dividing said signal averaged QRS signal into a sequence of overlapping time segments each have a plurality of data points, for transforming said data points of each of said time segments into a matrix ofpower content indicators organized by time segment and frequency components, for correlating said power content indicators of said frequency components with said correlation upon successive time segments, for generating at least one spectral turbulence parameter based upon the correlation of successive time segments with said at least one abnormality indication based upon the value of said at least one spectral turbulence parameter.

29. A system for detecting heart conditions comprising
first means for receiving at least one QRS signal,
second means for generating at least one abnormality indication, said second means connected to said first means, said second for dividing said at least one QRS signal into a sequence of overlapping time segments each have a plurality of data points, for transforming said data points of each of said time segments into a matrix ofpower content indicators organized by time segment and frequency components, for correlating said power content indicators of said frequency components with said correlation upon successive time segments, for generating at least one spectral turbulence parameter based upon the correlation of successive time segments with said at least one abnormality indication based upon the value of said at least one spectral turbulence parameter, and
third means for displaying said at least one abnormality indicator.

30. A system for detecting heart conditions comprising
a scanner adapted to receive Holter tapes storing a sequence of QRS signals, said scanner for scanning said tapes at high speed,
a digital to analog converter for converting said QRS signal into digital type signal suitable for storing in a digital computer having memory,
digital computer for generating at least one abnormality indication, said digital computer connected to a memory storing said converted QRS signal, said digital computer for dividing said at least one QRS signal into a sequence of overlapping time segments each have a plurality of data points, for transforming said data points of each of said time segments into a matrix ofpower content indicators organized by time segment and frequency components, for correlating said power content indicators of said frequency components with said correlation upon successive time segments, for generating at least one spectral turbulence parameter based upon the correlation of successive time segments with said at least one abnormality indication based upon the value of said at least one spectral turbulence parameter.

31. The system of claim 30 further comprising display means for displaying to an operator said at least one abnormality indicator.

32. The system of claim 30 further comprising
Holter recorder means worn by a patient to record the patient's QRS signal on Holter magnetic tape, and
Holter magnetic tape suitable for storing analog QRS signal over an ambulatory period.

33. The system of claim 30 wherein said display means is a CRT connected to said digital computer.

34. The system of claim 30 wherein said display means is a printer connected to said digital computer.

35. An apparatus for providing an indicator of electrical heart conduction, said apparatus comprising means for receiving QRS signal from a human being, electronic filters for isolating frequency components of said QRS signal, comparators for comparing isolated frequency components at intervals over said QRS signal, and electronic circuit connected to comparators for generating an indication of spectral turbulence.

* * * * *